US00PP13126P2

(12) United States Plant Patent
Stemkens

(10) Patent No.: US PP13,126 P2
(45) Date of Patent: Oct. 22, 2002

(54) VERBENA PLANT NAMED 'OXENA'

(75) Inventor: Henricus G. W. Stemkens, Hoorn (NL)

(73) Assignee: Syngenta Seeds B.V. (NL)

( * ) Notice: Subject to any disclaimer, the term of this patent is extended or adjusted under 35 U.S.C. 154(b) by 0 days.

(21) Appl. No.: 09/819,500

(22) Filed: Mar. 28, 2001

(51) Int. Cl.[7] ..... A01H 5/00
(52) U.S. Cl. ..... Plt./308
(58) Field of Search ..... Plt./308

(56) References Cited

PUBLICATIONS

UPOV–ROM GTITM Computer Database 2001/06, GTI Jouve Retrieval Software, Citation for Verbena 'Oxena'.*

* cited by examiner

*Primary Examiner*—Bruce R. Campell
*Assistant Examiner*—June Hwu
(74) *Attorney, Agent, or Firm*—Bruce Vrana

(57) ABSTRACT

A new Verbena plant particularly distinguished by its red-rose flower, early flowering, a spreading habit that is first semi-erect and later spreading.

1 Drawing Sheet

LATIN NAME OF THE GENUS AND SPECIES OF THE CLAIMED PLANT

*Verbena×hybrida.*

VARIETY DENOMINATION

'Oxena'.

BACKGROUND OF THE NEW PLANT

The present invention comprises a new distinct cultivar of Verbena, botanically known as *Verbena×hybrida*. The new cultivar is propagated from cuttings resulting from the cross of 'Z752' and 'Z744'. 'Z752' is a scarlet flowering Verbena having a spreading habit. 'Z752' is not commercially available and is not known by any synonyms. 'Z744' is a rose flowering Verbena having a semi-erect habit. 'Z744' is not commercially available and is not known by any synonyms. Neither 'Z752' or 'Z744' has been patented. As a result of this cross the present cultivar was created in 1997 in Enkhuizen, Netherlands and has been repeatedly asexually reproduced by cuttings in Enkhuizen, Netherlands and Sarrians, France over a three year period. It has been found to retain its distinctive characteristics through successive propagations, and this novelty appears to be firmly fixed.

This new Verbena plant is an annual in most climatical zones in the US, only in zones 9 and 10 it is a perennial plant.

DESCRIPTION OF THE DRAWING

The new Verbena plant is illustrated by the accompanying photographic drawing which shows blooms, buds and foliage of the plant in full colour, the colour shown being as true as can be reasonably obtained by conventional photographic procedures.

DESCRIPTION OF THE NEW CULTIVAR

The following detailed descriptions set forth the distinctive characteristics of this new Verbena. The data which defines these characteristics were collected from asexual reproductions carried out in Enkhuizen, Netherlands. The plant history was taken on 14 weeks old plants, blossomed under natural light in a greenhouse. Colour readings were taken in the greenhouse under ambient light. Colour references are primarily to The R.H.S. Colour Chart of The Royal Horticultural Society of London.

Differences between the new variety 'Oxena', its parents and a similar cultivar

| Character | 'Oxena' | 'Z752' | 'Z744' | 'Aztec Red' |
|---|---|---|---|---|
| Flower Color | Rosy red | Scarlet | Rose | Scarlet |
| Leaf Margin | To double incised | Double incised | Serrate | Serrate |
| Earliness | Early | Very early | Late | Late |

THE PLANT

Parentage:

*Female parent.*—A seedling named 'Z752' is one of our seedlings from our Z-generation of plants bred in 1996.

*Pollen parent.*—A seedling named 'Z744' is one of our seedlings from our Z-generation of plants bred in 1996.

Growth habit: Semi-erect later spreading.
Plant height: 19–28 cm.
Spreading area of plant: 40–80 cm.
Growth rate: Hanging and vigorous.
Heat and cold resistance: Resistant to hot and cold weather.
Branching character: Freely branching and lateral branching at every node.
Blooming period: From April till November.

THE STEM

Diameter: 2–2.5 mm.
Shape: Tetragonal.
Anthocyan pigmentation: Absent.
Length of internode: 20–50 mm, depending on the light where the plant is propagated.
Pubescence: Pubescence is present.

THE FOLIAGE

Phyllotaxis: Opposite.
Shape of blade: Broadly ovate, pinnatisect.

Texture:
*Upper side.*—Smooth.
*Lower side.*—Smooth.
Venation: Pinnate.
Leaf margin: Simple to double incised.
Leaf base: Truncate.
Leaf apex: Acute.
Length: 20–50 mm.
Width: 18–40 mm.
Depth of incision: 5–18 mm.
Colour:
*Upper side.*—Dark green 137A.
*Lower side.*—Light green 138A.
Pubescence: Some pubescence is present.
Length of leaf stem: 5–15 mm.
Petiole surface structure: Slightly pubescent.

THE BUD

Peduncle length: 40–80 mm, depending on season.
Size:
*Diameter.*—2 mm.
*Length.*—8–12 mm.
Shape: Elongated and ovate.
Colour: Medium green 137D.
Sepals:
*Colour.*—Light green 138B.
*Form.*—Upright.
*Number.*—5, fused.
*Size.*—5 mm.
*Shape.*—Elongated.

THE FLOWER

Direction: Ascending.
Diameter: 16–22 mm.
Height: 16–18 mm.
Borne: In a cluster.
Form: Salverform; sessile on terminal spikes.
Cluster: Spike.
Colour: Rosy-red 45B, more purple towards center.
Eye: A very small (2 mm) Pinkish Eye (69D) is present Typically three out of the five petals exhibit this pinkish coloration.
Overlapping of petals: Separate.
No. of petals: Gamopetalous, 5 lobed.
Shape of the petals: Each petal is heart shaped at the apex and grown together at base of petal.
Petal margin: Entire.
Petal surface texture: Smooth.
Size of the petal:
*Length.*—7–9 mm.
*Width.*—7–9 mm.
Spike:
*Length.*—20–35 mm.
*Diameter.*—20–35 mm.
Calyx length: 8–10 mm.
Anthocyan pigmentation of calyx limb: Absent.
No. of flowers per spike: 20–30.
Fragrance: No fragrance.
Lastingness of bloom: New florets continue to open in one spike over a period of 16 days.

REPRODUCTIVE ORGANS

One pistil and 4 stamens in pairs; colour for both is yellowgreen 145D. The pistil is 16–18 mm long. Pollen is not present. The filaments and anthers are fused to the corolla. The anthers are enclosed and not a prominent feature of the flower. 'Oxena' does not freely set seed.

ROOTS

Type of roots: Fibrous. Roots start to grow on every part of the stem that contacts the soil, so not only at the nodes.

PHYSIOLOGICAL AND ECOLOGICAL CHARACTERISTICS

Good tolerance to heat and cold. Strong resistance to pests and diseases, particularly powdery mildew.

We claim:

1. A new and distinct variety of Verbena plant, substantially as herein illustrated and described, characterized particularly as to novelty by larger red-rose flowers, which appear earlier on the plant, and a growing habit that is first semi-erect but later spreading.

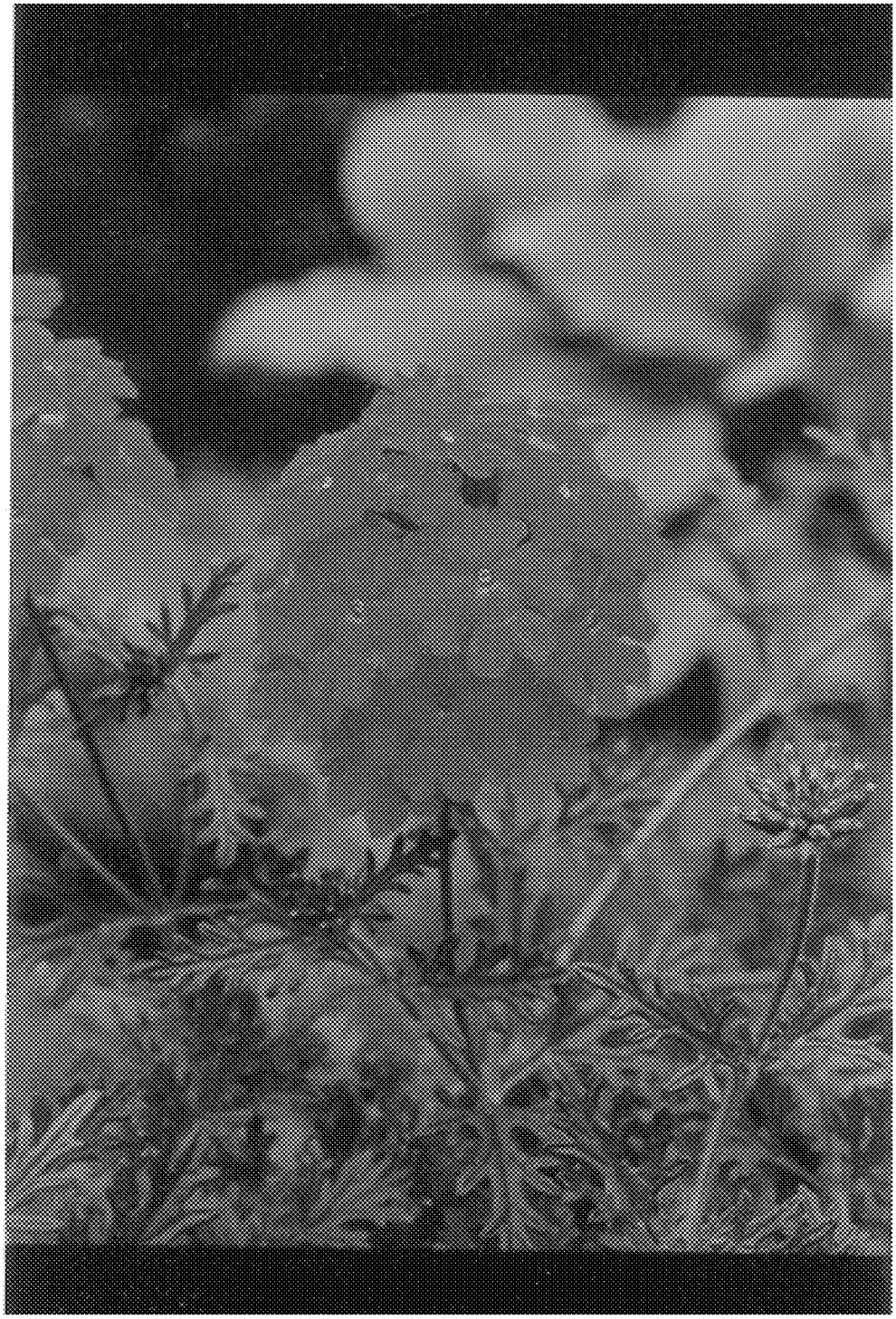

* * * * *